(12) United States Patent
Wright (10) Patent No.: US 6,187,040 B1
(45) Date of Patent: Feb. 13, 2001

(54) MITRAL AND TRICUSPID ANNULOPLASTY RINGS

(76) Inventor: John T. M. Wright, 555 S. Downing St., Denver, CO (US) 80220

( * ) Notice: Under 35 U.S.C. 154(b), the term of this patent shall be extended for 0 days.

(21) Appl. No.: 09/303,864

(22) Filed: May 3, 1999

(51) Int. Cl.$^7$ .................................................. A61F 2/24
(52) U.S. Cl. ........................................................ 623/2.36
(58) Field of Search ................................. 623/2.36, 2.37

(56) References Cited

U.S. PATENT DOCUMENTS

| | | | |
|---|---|---|---|
| 4,042,979 | * | 8/1977 | Angell . |
| 4,164,046 | * | 8/1979 | Cooley ................................. 623/2.36 |
| 4,917,698 | * | 4/1990 | Carpentier ............................ 623/2.36 |
| 5,061,277 | * | 10/1991 | Carpentier ............................ 623/2.36 |
| 5,064,431 | * | 11/1991 | Gilbertson ............................ 623/2.37 |
| 5,104,407 | * | 4/1992 | Lam ...................................... 623/2.36 |
| 5,201,880 | * | 4/1993 | Wright .................................. 623/2.37 |
| 5,306,296 | * | 4/1994 | Wright .................................. 623/2.37 |
| 5,607,471 | * | 3/1997 | Seguin .................................. 623/2.36 |
| 5,628,790 | * | 5/1997 | Davidson .............................. 623/2.36 |
| 5,674,279 | * | 10/1997 | Wright .................................. 623/2.37 |
| 5,824,066 | * | 10/1998 | Gross .................................... 623/2.36 |

* cited by examiner

Primary Examiner—Michael J. Milano (57) ABSTRACT

Flexible annuloplasty ring having internal close coiled helical spring embodied, inter alia, in a mitral ring having a curved semi-flexible stiffener member in the anterior segment to maintain intertrigonal distance during implantation, the plane of the anterior segment lying at an arc configuration of about 30°–75° to the plane of the posterior segment, arcing up across the anterior leaflet to prevent outflow tract obstruction.

15 Claims, 4 Drawing Sheets

MITRAL AND TRICUSPID ANNULOPLASTY RINGS

FIELD OF THE INVENTION

This invention relates to prosthetic annuloplasty rings for use in the surgical correction of some defects of the two atrio-ventricular valves in the human heart.

BACKGROUND OF THE INVENTION

The mitral valve lies in the left side of the heart and the tricuspid valve in the right. These valves, especially the mitral valve, if significantly damaged require repair or replacement. The normal mitral and tricuspid valves have different anatomy the annulus of mitral valve is somewhat "D" shaped, while the annulus of the tricuspid valve is more nearly circular. Valve dysfunction can lead to stenosis a restriction to flow or regurgitation, or both.

A surgically repairable valve often has a dilated annulus. This dilatation may prevent full coaptation of valve leaflets, while an asymmetrical annular dilatation may result in incomplete leaflet coaptation and hence leakage of the valve. Consequently, most repair procedures involve remodeling and stabilization of the annulus by implanting an annuloplasty ring to reduce in the overall size of the valve annulus. When repairing the mitral repairs it is necessary to preserve the normal distance between the two fibrous trigones located adjacent to the anterior leaflet. In this region a definitive annulus is absent. Alteration of the inter-trigonal distance could lead to distortion of the aortic valve with possible aortic regurgitation or left ventricular outflow obstruction. Thus an effective annuloplasty ring should ensure that the natural inter-trigonal distance is neither increased nor diminished by the valve repair procedure.

The prior art regarded as most pertinent to the present invention is incorporated herein by reference to provide a comprehensive background setting to enable better understanding of the present invention and its advantages. The incorporated prior art is tabulated hereinafter, and the features of the prior art considered most closely related to the problems faced in the prior art that are overcome by the present invention are discussed in some detail hereinafter.

Various prostheses have been described for use in conjunction with mitral or tricuspid valve repair. Each has disadvantages. The ring developed by Dr. Alain Carpentier U.S. Pat. No. 3,656,185 is rigid and flat. Although widely used, criticism of its inflexibility preventing the normal alteration in size and shape of the mitral annulus with the cardiac cycle has been widespread. The complication of left ventricular outflow tract obstruction has been described in association with this device. This complication can take the form of a decrease in the dimensions of the left ventricular outflow tract, or systolic anterior motion of the anterior leaflet of the valve. Both complications were reported by Geller M, Kronzon I, Slater J et al. "Long-term follow-up after mitral valve reconstruction: incidence of postoperative left ventricular outflow obstruction". Circulation 1986;74 supp. I I-99–103. They implanted Carpentier rings in sixty-five patients. All sixty surviving patients were restudied 1–55 months postoperatively. All showed a significant decrease in the dimensions of the left ventricular outflow tract, and 6 patients 10% also had systolic anterior motion SAM. Another complication of the Carpentier ring has been inflow obstruction. This complication associated with its use in tricuspid valves was reported by Carpentier et al. in nine of seventeen patients Carpentier A, Deloche A, Hanania G, et al. "Surgical management of acquired tricuspid valve disease". J Thorac Cardiovasc Surg 1974;67:53–65. In addition, the Carpentier ring has the disadvantage of not being of adjustable size. Thus the surgeon has to accurately judge the correct size of ring needed to reduce the annulus size and produce a competent valve.

An open ring valve prosthesis was described in U.S. Pat. No. 4,164,046 comprising a uniquely shaped open ring valve prosthesis having a special velour exterior for effecting mitral and tricuspid annuloplasty. This ring was not adjustable in size during or following implantation. The fully flexible annuloplasty ring described by Carlos D. Duran and Jose Luis M. Ubago, "Clinical and Hemodynamic Performance of a Totally Flexible Prosthetic Ring for Atrioventricular Valve Reconstruction" Annals of Thoracic Surgery, No.5, 458–463, November 1976 could only be shortened in the posterior segment by the placement of plicating sutures. The judgement of the position, size and spacing of these sutures requires skill and experience. However, inappropriate suture placement in the anterior segment could cause undesirable intra-trigonal shortening. Adjustable annuloplasty rings were described by Dr. William Angell U.S. Pat. No. 4,042,979 and Dr. Miguel Puig-Massana U.S. Pat. No. 4,290,151. Both incorporate drawstrings capable of reducing the size of the posterior portion of the ring. The former contains a rigid or flexible member in the anterior leaflet portion of the ring. The latter ring is also adjustable but fully flexible. With this device the use of a continuous implantation suture was recommended rather than the more generally used interrupted sutures. With the Puig-Massana ring the use of interrupted sutures would be likely to interfere with the internal drawstrings. However, should a continuous suture be used for implantation, and the ring then contracted by the internal drawstrings, loosening of the continuous suture would be caused by the reduction in the circumference of the annulus. A further disadvantage of Puig-Massana's ring is that following the tightening of the drawstrings, a bulky knot is formed on the atrial surface of the ring. Hence, the knot lies in the direct blood flow path into the inflow of the valve. Should a thrombus form on the knot it could later embolize. In addition, should the surplus drawstrings be cut too close to the knot, there is the danger of the knot becoming undone. Conversely, should significant surplus drawstrings tails remain, abrasion of the valve leaflets could occur. The adjustable ring by Dr. Ali Ahmadi has the disadvantage of being circular, which is not an appropriate shape, particularly for the mitral annulus.

The rigid rings described above were probably conceived on the assumption that the mitral annulus is "D" shaped and lies in a single flat plane. That this was a misconception was shown by Levine, R. A., Triulzi, M. O., Harrigan P., and Weyman,A. E. "The relationship of mitral annular shape to the diagnosis of mitral valve prolapse", Circulation 75, No. 4, 756–767, 1987. This work shows that the mitral valve annulus is a complex and mobile structure and demonstrated that the mitral valve takes the form of a central, elliptical portion of a hyperbolic paraboloid or saddle shaped surface. It is clear that imposing a flat ring or even a segment of a flat ring would distort the annulus and could cause left ventricular outflow tract obstruction.

Wright and Elliott, U.S. Pat. No. 5,674,279, describe annuloplasty and suture rings in the form of adjustable, flexible tricuspid and tricuspid annuloplasty rings having internal drawstrings that merge from the rings on the annular faces so that the drawstring knots are out of the bloodstream. The drawstrings are contained in clearly marked channels. The mitral ring has a curved semi-flexible stiffener member in the anterior segment to maintain intertrigonal distance during implantation. While the Wright and Elliott device solved many of the problems inherent in the prior art devices, there remains a need for flexible tricuspid and tricuspid annuloplasty rings that assure that the orifice defined by the ring remains substantially constant in cross-section without undue interference with the movement of the surrounding tissue.

The present invention is embodied in annuloplasty ring structure that in large measure overcome the disadvantages of the prior art and provides improved performance and reliability.

It is an objective of this invention to provide a fully flexible, annuloplasty rings specific for use in mitral and tricuspid valve repair.

It is a further objective of this invention to provide a mitral annuloplasty ring in which the inter-trigonal distance and anterior segment is maintained during implantation.

It is a further objective of this invention to provide an annuloplasty ring which is flexible yet which resists plication (puckering) by the action of the implantation sutures.

It is a further objective of this invention to provide a mitral annuloplasty ring that is flexible in an undulating manner so as to follow the change in shape of the mitral annulus, in the plane of the annulus.

It is a further objective of this invention to provide a mitral annuloplasty ring that is flexible about the posterior portion of its circumference, and that prevents restriction of the left ventricular outflow tract.

It is a further objective of this invention to provide a mitral annuloplasty ring that is flexible about the anterior portion of its circumference, and that prevents restriction of the left ventricular outflow tract.

It is a further objective of this invention to provide an annuloplasty ring that is technically easy to use.

Other objectives and advantages of this invention will be more apparent from the detailed description of the device which follows.

SUMMARY OF THE INVENTION

This invention relates to flexible atrio-ventricular annuloplasty ring incorporating a circumferential string and one or more light, closely wound helical metallic spring members through which said string passes. In a preferred embodiment of the invention, one spring is situated in a substantial portion of one segment of the ring, and other like springs are situated in the second and third segments of the ring. When such ring is implanted in the mitral annulus, the first segment of the ring containing the spring will correspond to the anterior segment of the annulus. Likewise the second and third segments of the ring containing like springs will be implanted such that said second and third segments correspond to right and left segments of the posterior annulus respectively. When said ring is implanted in the tricuspid annulus, the first segment of the ring will be implanted in the posterior segment of the tricuspid annulus.

In an alternative embodiment of the invention, one spring is situated in a substantial portion of the first segment, and elastomeric radiopaque members are situated in the second and third respectively through which said string pass. When such a ring is implanted in the mitral annulus, the first segment of the ring containing the spring will correspond to the anterior segment of the annulus. Likewise the second and third segments of the ring containing radiopaque members in said second and third segments will be implanted such that said second and third ring segments correspond to right and left segments of the posterior mitral annulus respectively. When said alternative embodiment of said ring is implanted in the tricuspid annulus, the first segment of the ring containing the spring will correspond posterior segment of the tricuspid annulus. In mitral valve surgery, the first segment spring member serves to prevent shortening intratrigonal and anterior leaflet distance by plication of the ring, and hence of the annulus, during implantation. The anterior segment of the ring is intended to be sutured in a curved arc across the sub-aortic curtain of the atrial wall of the aortic outflow tract. In a preferred embodiment of the invention the close coiled springs contained in the said second and third segments of the ring will also prevent shortening of the annulus by plication.

In one preferred embodiment of the invention the flexible body of the ring is of an symmetrical biocompatible tube formed from extruded and expanded polytetrafloroethylene. In an alternative embodiment the flexible body of the ring is of a asymmetrical biocompatible tube formed from extruded and expanded polytetrafloroethylene. In a further alternative embodiment of the invention the biocompatible body is formed of braided, knitted or woven DACRON® polyethylene teraphthalate, or other biocompatible fibrous material, formed into tubular form. The body of the further alternative embodiment of the invention may be substantially circular or oval in cross-section.

The preferred annuloplasty ring comprises an elongate tube of suturable material, an elongate tubular flexible non-contractile member, preferably in the form of a close coiled biocompatible spring member in tube, the spring member having first and second ends and defining a passage there through, a string extend through passage in the spring and means securing the string proximate said ends of the for preventing extension of the. The spring and string are configured and constructed and secured together to allow the ring define an arc corresponding, in use, to the curved anterior segment of the mitral valve annulus and to permit the shape to vary during the cardiac cycle without extension or compression of the arc length. The annuloplasty ring is suitable for use in repair a patient's mitral valve annulus, said mitral valve annulus comprising anterior and posterior segments., the tube and spring being configured and constructed to encompass, in use, at least a substantial part of the anterior segment of the mitral valve annulus. In a preferred embodiment, the spring and string are configured and constructed and secured together to define an arc configuration corresponding, in use, to the curved anterior segment of the mitral valve annulus and to permit said arc configuration to vary during the cardiac cycle without extension of the.

Generally, the annuloplasty ring may comprise an elongate tube of suturable material, an elongate tubular flexible non-contractile member configured and constructed to define a passage there through in said tube, said member having first and second ends and defining a passage there through, a string extend through said passage in said non-contractile member, and means securing the string proximate said ends of said non-contractile member for preventing extension of said elongate tubular flexible non-contractile member. The elongate tubular flexible non-contractile member and string are configured and constructed and secured together to define an arc configuration corresponding, in use, to the curved anterior segment of the mitral valve annulus and to permit said arc configuration to vary during the cardiac cycle without extension of said elongate tubular flexible non-contractile member. The valve may be configured and constructed to be used in the repair of a patient's mitral valve annulus that comprises anterior and posterior segments, the annuloplasty ring comprising an elongate tube of suturable material, an elongate tubular flexible, non-contractile member configured and constructed to define a passage there through in said tube, said elongate tubular flexible non-contractile member having first and second ends and defining a passage there through, a string extend through said passage, and means securing the string proximate said ends of said elongate tubular flexible non-contractile member for preventing extension of said elongate tubular flexible non-contractile member, said tube and elongate tubular flexible non-contractile member being configured and constructed to encompass, in use, at least a substantial part of the anterior segment of the mitral valve annulus.

BRIEF DESCRIPTION OF THE DRAWINGS

The present invention may be better understood and the advantages will become apparent to those skilled in the art by reference to the accompanying drawings, wherein like reference numerals refer to like elements in the several Figures, and wherein.

DESCRIPTION OF THE PREFERRED EMBODIMENTS

This invention is directed to a fully flexible, atrio-ventricular annuloplasty ring containing a circumferential internal string which passes though the lumen of a substantially non-compressive close coiled helical spring member which is located in a least one segment of the ring.

In a preferred embodiment of the invention, when used in the mitral valve, one flexible but in expansible and incompressible portion of the prosthesis is formed to fit about the base of the anterior leaflet of the valve, and second and third portions flexible but in expansible portions of the prosthesis are formed to fit about the base of the left and right segments of the posterior annulus leaflet of the valve. A flexible close coiled helical spring member located in the anterior portion of the prosthesis is to maintain the natural geometry of the anterior segment during and following implantation. The flexible nature of the spring allows the anterior segment containing the spring to follow a curved path on an inclined plane on the sub aortic curtain above the so called annulus of the anterior leaflet, and to follow any natural motion of the base of the aortic valve. Colored marking sutures in the anterior segment of the device serve to mark the two locations of the ring that are intended to lie adjacent to the natural tissue trigons of the anterior portion of the natural annulus. These colored marking sutures may, in an alternative embodiment of the device, serve to anchor and stabilize an internal string of the device.

The flexible member that is non-compressive and rendered inextendable by an internal string, knotted at either end of the helical spring. The close coiled helical spring forms a radiopaque member. The string maintains the natural geometry of the intra-trigonal and/or intra-commisural anterior leaflet distance when said ring is implanted in the mitral position. At the same time the annuloplasty ring provides adequate strength and flexibility and limited tissue in growth potential yet permits a low needle penetration force for convenience of implantation. A particular advantage of this construction is that there are no portions of the extruded and expanded material of the body that might fray, and that the joint line is so placed within the ring is not subject to stresses. The body is substantially circular in cross-section.

The flexible body of the ring is of a biocompatible material, preferably of an extruded and expanded polyethertetraphylate tubular material. The construction of the annuloplasty ring is such that it is relatively simple to manufacture. The ring contains radiopaque materials so that postoperative radiopaque assessment is simplified.

Figures 1, 2, 3, 4, 5:
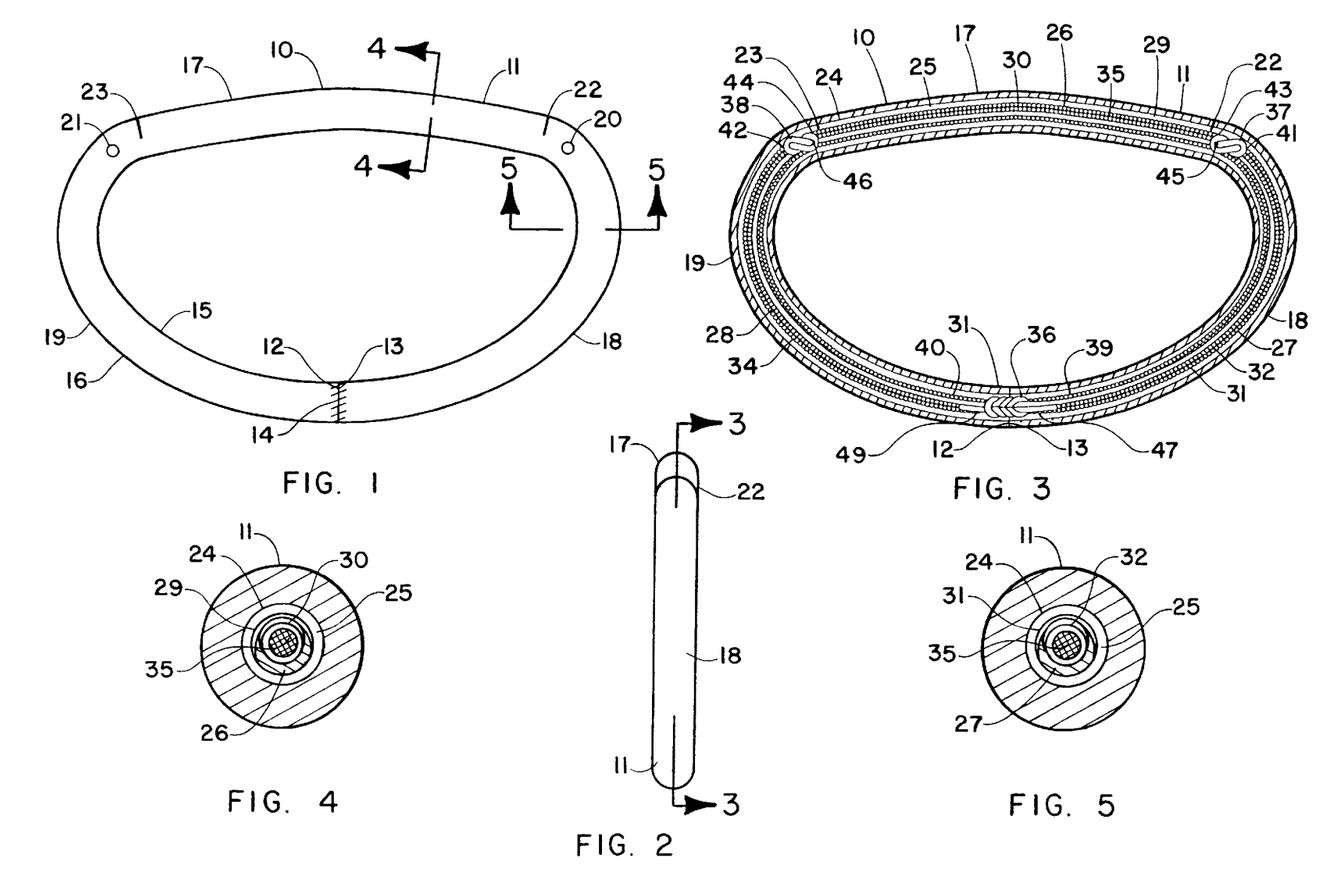
FIG. 1 shows a plan view from the atrial aspect of the closed ring.
FIG. 2 shows a side elevation view of the closed ring., i.e., the closed ring of FIG. 1 viewed from the right side as depicted in the drawing.
FIG. 3 shows a cross-sectional view of a preferred embodiment of the closed ring taken along line 3—3 of FIG. 2.
FIG. 4 shows a cross-sectional view of a preferred embodiment of the closed ring taken along line 4—4 of FIG. 1.
FIG. 5 shows a cross-sectional view of a preferred embodiment of the closed ring taken along line 5—5 of FIG. 1.

Referring now to FIG. 1 and FIG. 2, the device 10 is composed of a single flexible cylindrical tube 11, which has its ends 12, 13 sewn together by suture 14 to form a flattened ring having an inner periphery 15 and an outer periphery 16. The ring has three segments 17, 18, 19. The following nomenclature will apply to the ring as it is to be implanted in the mitral annulus of a patient. Segment 17 is designated as the anterior segment, segment 18 the right posterior segment, and segment 19 the left posterior segment. At the junction of the anterior segment 17 and the right posterior segment 18 is a colored marker 20. This mark is intended to lie adjacent to the natural tissue of the right commissural portion of the natural annulus. At the junction of the anterior segment 17 and the left posterior segment 19 is a colored marker 21. This mark is intended to lie adjacent to the natural tissue of the left commissural portion of the natural annulus. Approximately 3 mm from the right commissural marker 20 and in the anterior segment 17 is located a colored suture 22 which forms the right trigon marker. Approximately 3 mm from the left commissural marker 21 and in the anterior segment 17 is located a colored suture 23 which forms the left trigon marker.

Referring now to FIG. 4 it will be noted that tubular body 11 has inner wall 24, defining inner space 25. Contained in the space 25 within inner wall 24 is a close coiled helical springs 26. This spring is preferably wound from a biocompatible metal such an Carpenter NP35N alloy. The spring is preferably wound using 0.010–0.012 inch diameter wire, although other wire diameters in the range 0.005–0.020 inches are possible. Spring 26 lies in the anterior segment 17 of the ring. Anterior segment spring 26 has an outer diameter 29 and an inner diameter 30. The inside diameter is approximately 0.035 inches, and the outside diameter is approximately 0.055 inches.

Referring now to FIG. 5 it will be seen that spring 27, which is a close coiled helical spring such as the spring 26 just described, lies in the right posterior segment 18 of the ring. A mirror image of the structure shown in FIG. 5 is found on the left of the structure depicted in FIGS. 1–3, wherein a like spring 28 lies in the left posterior segment 19 of the ring.

Likewise, right and left posterior springs 27 and 28 have an outer diameter and an inner diameter preferably corresponding to like diameters of spring 26. A single string 35, monofilament or multifilament, lies within the inner diameters of springs 26, 27, 28 respectively. This string 35, which is preferably of a size 1 braided polyester surgical suture, is terminated in a secure knot 36. The string also has two simple knots preferably "Figure of eight knots" 37, 38. String termination knot 36 lies approximately straddling tube ends 12, 13 within tube seam formed by suture 14, and between one end 39 of right posterior segment spring 27 and one end 40 of left posterior segment spring 28. The overall diameter of termination knot 36 is larger than the inner diameter 32 of right posterior segment spring 27 and larger than the inner diameter 34 left posterior segment spring 28. The simple knot preferably "a Figure of eight knot" 37 of string 35 lies immediately adjacent and between end 41 of right posterior segment spring 27 and end 43 of anterior segment spring close coiled helical spring 26. Likewise the simple knot preferably "a Figure of eight knot" 38 of string 35 lies immediately adjacent and between end 42 of left posterior segment spring 28 and end 44 of anterior segment spring close coiled helical spring 25. The overall diameter of simple knots 37, 38 are larger than the inner diameter 30 of anterior segment spring 26 and inner diameters 32 of right posterior segment spring 27 and inner diameter 34 left posterior segment spring 28.

Right trigon suture marker 22 passes internally through tube 11 and through internal string 35 at 45 adjacent to knot 37 and likewise left trigon suture marker 23 passes internally through tube 11 and through internal string 35 adjacent to knot 38 at 46. Thus the overall size of knots 36, 37, 38 relative to the inner diameter 30 of anterior segment spring 26 and inner diameter 32 of right posterior spring 27 and inner diameter 34 left posterior spring 28, combined with right and left trigon sutures engaging with string 35 at points 45, 46 prevent radial migration of string 35 and spring 26 relative to tube 11, and also prevent radial migration towards the anterior segment 17 of right segment spring 27 and left segment spring 28 towards the anterior segment 17 of ring 10.

Figures 6, 7, 8, 9, 10:
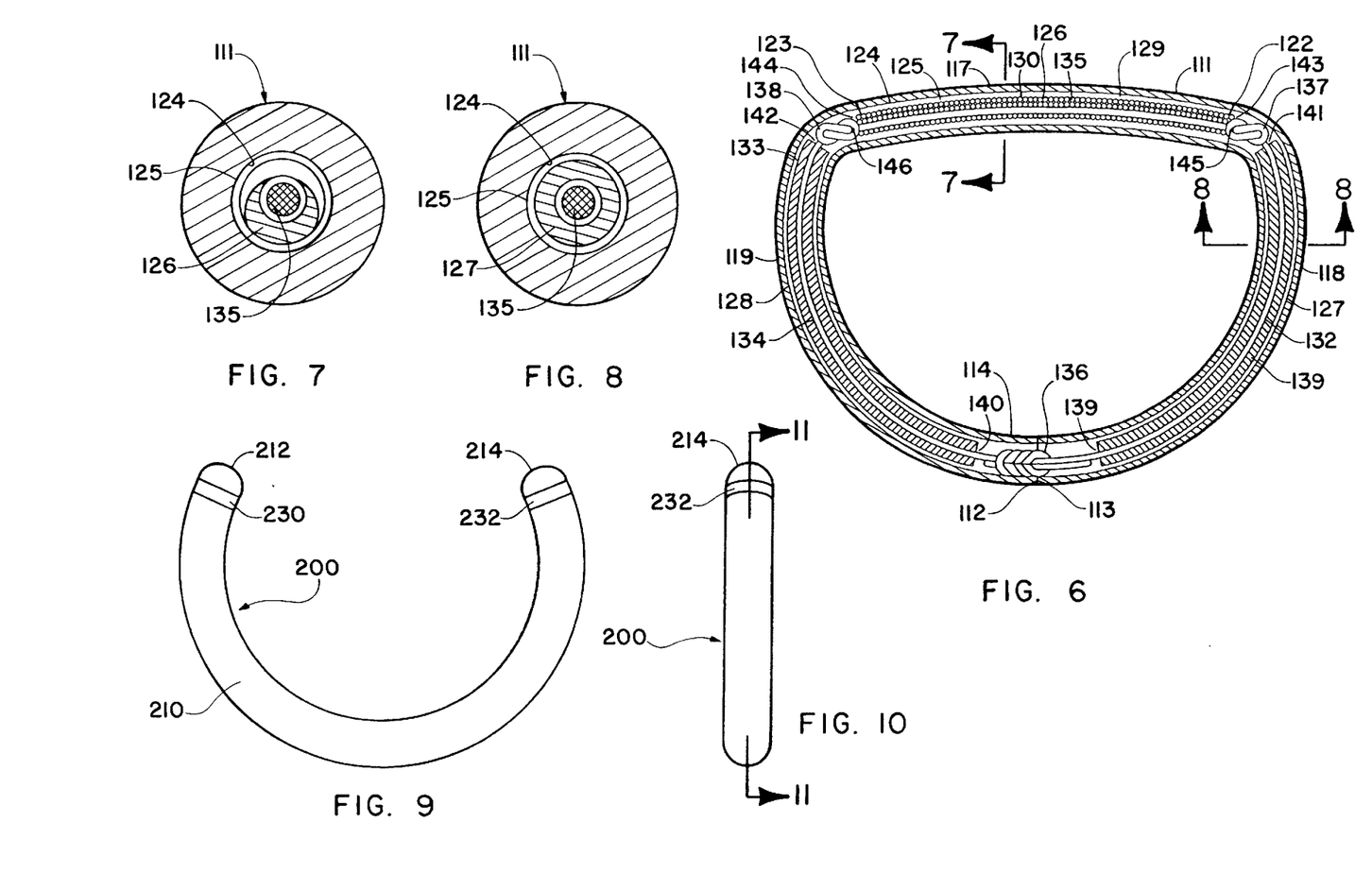
FIG. 6 shows a cross-sectional view of an alternative embodiment of the closed ring invention, the cross-section corresponding to the cross-section taken in a plane corresponding to that shown in FIG. 3.
FIG. 7 shows a cross-sectional view of the alternative embodiment of the closed ring depicted in FIG. 6, taken along lines 7—7 of FIG. 6.
FIG. 8 shows a cross-sectional view of the alternative embodiment of the closed ring depicted in FIG. 6, taken along lines 8—8 of FIG. 6.
FIG. 9 shows a plan view from the atrial aspect of a further alternative embodiment is which the ring is intended to support the posterior segment of the valve orifice.
FIG. 10 shows a side elevation view of the open ring shown in FIG. 9.

Reference is now made to FIGS. 6, 7 and 8, tubular body 111 has inner wall 124, defining inner space 125. Contained in the space 125 within inner wall 124 in the anterior segment 117 is a close coiled helical springs 126, preferably wound from a fatigue resistant, biocompatible metal such as Carpenter MP35N. The spring is preferably wound using 0.010–0.012 inch diameter wire, although other wire diameters in the range 0.005–0.020 inches are possible. Anterior segment spring 126 has an outer diameter 129, preferable of approximately 0.055 inches, and an inner diameter 130, preferable of approximately 0.035 inches. Contained in the space 125 within inner wall 124 in the right and left posterior segment 118, 119 are elongate tubular flexible non-contractile members such as flexible radiopaque tubes 127, 128, preferably of silicon elastomer impregnated with barium sulfate. Right posterior tube 127 has an outer diameter 131 preferably of approximately 0.055 inches and an inner diameter 132 preferably of approximately 0.035 inches, and left posterior tube 128 has an outer diameter 133 and an inner diameter 134. The inner and outer diameters of left posterior tube 128 is the same as that of right posterior tube 127. Lying within the inner diameter 130 of spring 126 and inner diameters 132, 134 of tubes 127, 128 is provided a single string 135. This string 135, which is preferably of a size 1 braided polyester surgical suture, is terminated in a secure knot 136. The string also has two simple knots preferably "Figure of eight knots" 137, 138. String termination knot 136 lies approximately straddling tube ends 112, 113 within tube seam formed by suture 114, and between one end 139 of right posterior segment tube 127 and one end 140 of left posterior segment tube 128. The overall diameter of termination knot 136 is larger than the inner diameter 132 of right posterior segment tube 127 and larger than the inner diameter 134 left posterior segment tube 128. The simple knot preferably "a Figure of eight knot" 137 of string 135 lies immediately adjacent and between end 141 of right posterior segment tube 127 and end 142 of anterior segment spring close coiled helical spring 126. Likewise the simple knot preferably "a Figure of eight knot" 138 of string 135 lies immediately adjacent and between end 142 of left posterior segment tube 128 and end 144 of anterior segment spring close coiled helical spring 126. The overall diameter of simple knots 137, 138 are larger than the inner diameter 130 of anterior segment spring 126 and inner diameters 132 of right posterior segment tube 127 and inner diameter 134 left posterior segment tube 128. Right trigon suture marker 122 passes internally through tube 111 and through internal string 135 at 145 adjacent to knot 137 and likewise left trigon suture marker 23 passes internally through tube 111 and through internal string 135 adjacent to knot 138 at 146. Thus the overall size of knots 136, 137, 138 relative to the inner diameter 130 of anterior segment spring 126 and inner diameter 132 of right posterior tube 127 and inner diameter 134 of left posterior tube 128, combined with right trigon suture 122 and left trigon suture 123, engaging with string 135 at points 145, 146 prevent radial migration of string 135 and anterior springs 126 relative to tube 111, and also prevent radial migration towards the anterior segment 117 of right segment tube 127 and left segment tube 128 towards the anterior segment 117 of ring.

Figure 11:
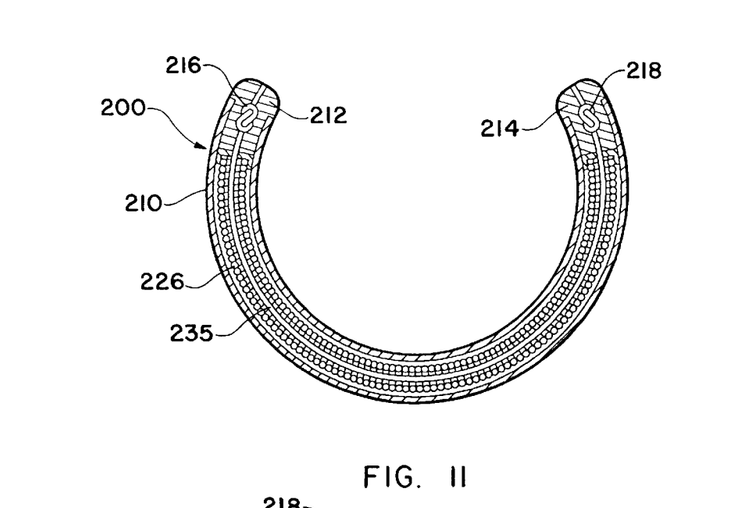
FIG. 11 shows a cross-sectional view the open ring depicted in FIGS. 9 and 10, taken along lines 11—11 of FIG. 10.

Referring now to FIGS. 9 through 12, a open suture ring of substantially similar construction is shown. The ring 200 comprises a tubular member 210 generally of the type previously described terminated at its respective ends by plugs 212 and 214. Colored sutures 230 and 232 are provided for identification and orientation. The plugs 212 and 214 are secured in position in the ends of the tube and provide securement of the ends by way of knots 216 and 218, respectively, as shown in FIG. 11, the right end, as depicted in FIG. 11, being shown in enlarged detail in FIG. 12. The plugs 212 and 214 may be of any suitable biocompatible material that can be punctured with a needle or formed in situ. Resilient polymers of many formulations can be used. The preferred material is self-vulcanizing silicone rubber, often referred to as RTV (room temperature vulcanizing) silicon rubber, which is easily and quickly formed in situ during fabrication. Enclosed inside the tube, in generally the same arrangement as described, is a non-expansible coiled spring 226 constrained non-extendably in the tube by string 235 as described in reference to the previous embodiments. An end cap, such as shown at 228, captures the end of the spring and rests against the end plug 214, like structure being found at the other end of the ring as well.

Figure 12:
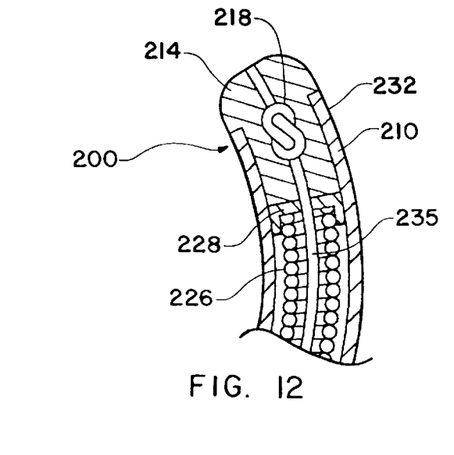
FIG. 12 shows an enlarged partial cross-sectional view of the open ring shown in FIG. 11, the cross-section corresponds to the cross-sectional view of FIG. 11, enlarged.
Figure 13:
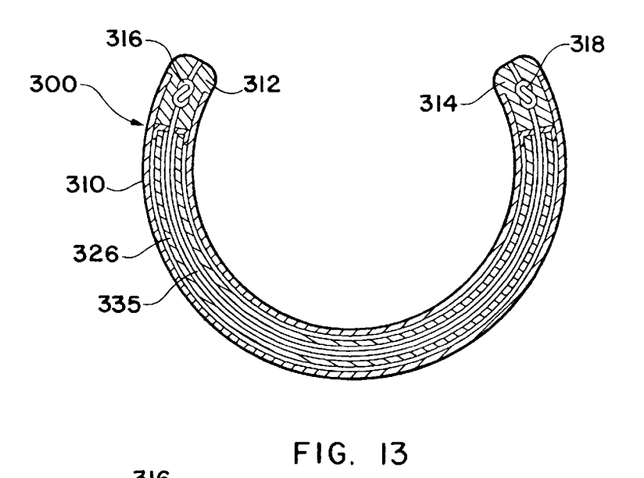
FIG. 13 shows a cross-sectional view another alternative embodiment of the closed ring, similar in overall configuration to that shown in FIG. 9, the cross-section corresponding to the cross-section taken in a plane corresponding to that shown in FIG. 11.
Figure 14:
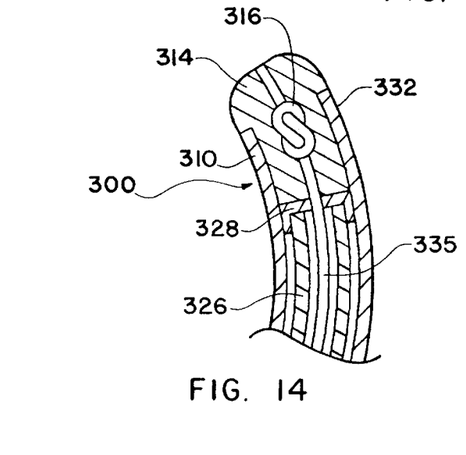
FIG. 14 shows an enlarged partial cross-sectional view of the further alternative embodiment of the open ring shown in FIG. 13, the cross-section correspond to the cross-sectional view of FIG. 13, enlarged.

The alternative embodiment of the ring 300 depicted in FIGS. 13 and 14 is structurally the same with the parts tube 310, plugs 312 and 314, knots 316 and 318 being substantially as described with the analogous structures in FIGS. 11 and 12. In this embodiment, however, the member 326, held by end caps 328 and secured by string 335 is a flexible radiopaque tubes, preferably of silicon elastomer impregnated with barium sulfate, of the type described in reference to FIGS. 6 and 8.

Figure 15:
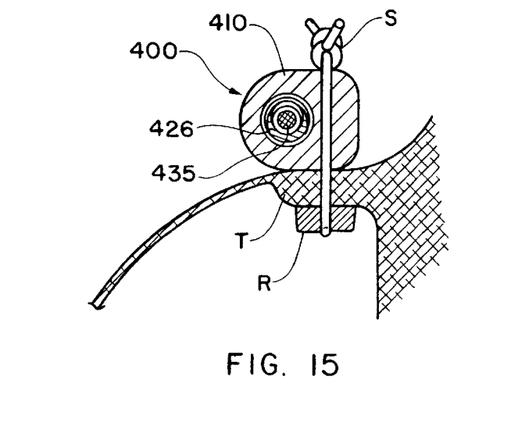
FIG. 15 shows a cross-sectional view of another alternative embodiment of the annuloplasty rings of this invention, showing and alternative suturing structure, sutured into the annulus of an atrio-ventricular valve.

Reference is made now to FIG. 15 which shows an enlarged cross-section view of a further alternative embodiment of the invention which may be embodied in rings of the type shown in any of preceding figures, differing only with respect to the outer tube construction. In suture rings 400 of this alternative embodiment, the outer ring 410 of the structure is formed in a "D" shape to provide additional material to be used in suturing the ring to the tissue T as shown, for example, by suture S. A reinforcing pledgit R may be used on the other side of the tissue T at the option of the surgeon. The suture knots may be positioned entirely outside the blood flow path, e.g. to the right of the "D" cross-sectional shaped ring 410 as shown in FIG. 15. As in the other embodiments, the ring comprises a non-extendable coil spring 426 secured against extension by a string 435. The ring is preferably made of expanded poly- tetra-flouroethylene in "D" shaped in cross-section, the face to the left in the Figure being, in use, the inner face forming the inside of ring, the opposing face forming the outside of ring 400. The cylindrical recess through which the non-expandable spring extends is radially displaced inwards towards the center of ring such that the outer wall thickness along the central axis is greater than inner wall thickness. As shown in FIG. 15, 5 the cylindrical recess contains the internal components of the ring previously described, such as close coiled helical spring 426 and string 435. The cylindrical recess is somewhat larger in diameter than that of the close coiled helical spring 426 to allow the internal components to slide into place without due interference with tubular body, and is preferable of approximately 0.060 inches diameter. The asymmetrical "D" shaped cross-section allows additional space for the needle of the implanting suture to pass on the portion of tube, relative to the use of the cylindrical member shown in the previously described embodiments. This additional material through which the implanting suture passes provides greater suture pull-out strength, and hence provides additional improved safety to the device. This is illustrated in FIG. 15, which shows the ring sutured onto the annulus of an atrio-ventricular valve of the heart. by a multiplicity of sutures, a portion of one of which is shown at S passing through the upper face of tube, through outer wall, through lower face and annulus, and typically into a reinforcing pledgit, lying adjacent to ventricular wall, thence back up through the ring to be secured by a knot.

Figure 16:
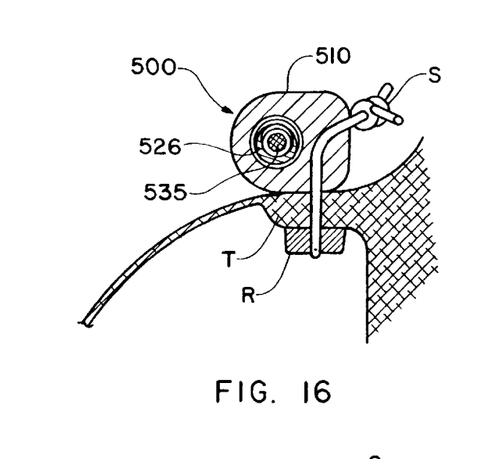
FIG. 16 shows a cross-sectional view of a different alternative embodiment of the annuloplasty rings of this invention, showing and alternative suturing structure, the suture knots being located on the outermost periphery of the annuloplasty ring, the ring being shown sutured into the annulus of an atrio-ventricular valve.

FIG. 16 depicts an annuloplasty ring 500 generally to the type shown in FIG. 15, components numbers 510, 526 and 535 corresponding components numbered 410, 426 and 435 shown in FIG. 15. Components R, S and T being as previously described. Note that the knot in the Suture S is on the outer periphery of the annuloplasty ring.

Figure 17:
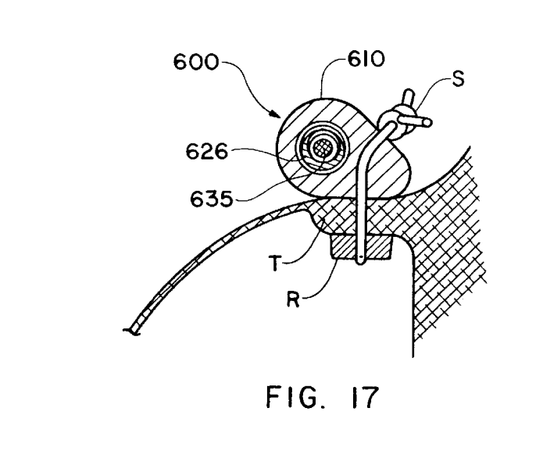
FIG. 17 shows a cross-sectional view of yet another alternative embodiment of the annuloplasty rings of this invention, showing and alternative suturing structure, the suture knots being located on an outer, thinner peripheral portion of the annuloplasty ring, the ring the ring being shown sutured into the annulus of an atrio-ventricular valve.

FIG. 17 depicts an annuloplasty ring 600 generally to the type shown in FIG. 15, components numbers 610, 626 and 635 corresponding components numbered 410, 426 and 435 shown in FIG. 15, except that the ring is constructed and configured to define the cross section 610 as comprising a thinner peripheral portion through which the suture extends. Components R, S and T being as previously described. Note that the knot in the Suture S is on the thinner periphery of the annuloplasty ring.

Figure 18:
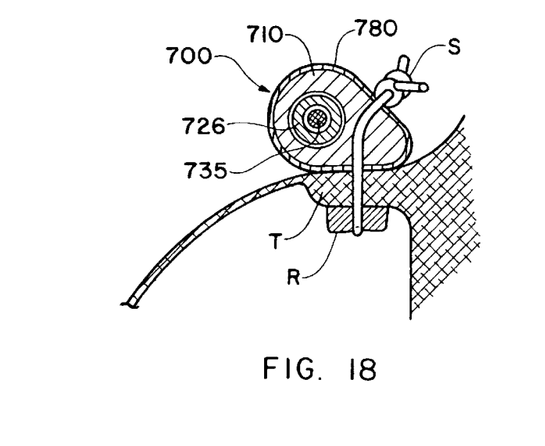
FIG. 18 shows a cross-sectional view of the alternative embodiment of the annuloplasty rings shown in FIG. 17, further improved by the addition of a very fine layer of biocompatible fabric to encourage tissue attachment to the annuloplasty ring of this invention, showing and alternative suturing structure, on an outer, thinner peripheral portion of the annuloplasty ring, the ring being shown sutured into the annulus of an atrio-ventricular valve.

FIG. 18 depicts an annuloplasty ring 700 generally to the type shown in FIG. 15, components numbers 710, 726 and 735 corresponding components numbered 410, 426 and 435 shown in FIG. 15, except that the ring is constructed and configured to define the cross section 710 as comprising a thinner peripheral portion through which the suture extends, such as depicted in FIG. 17, with the addition of a very thin layer 780 of biocompatible fabric, e.g. of DACRON® polyester fabric, over the TEFLON® expanded polytetrafluoroethylene (PTFE) of which the outer tube of the annuloplasty ring is made. This layer of fabric causes gives rise to tissue in growth and reduces the likelihood that thin layers of tissue may grow on the Expanded PTFE and slough off into the blood stream. Components R, S and T being as previously described. Note that the knot in the Suture S is on the thinner periphery of the annuloplasty ring. The annuloplasty ring of this embodiment is formed of an elongate tube of suturable expanded polytetrafluoroethylene material configured and constructed to define in cross-section an inner annular periphery having a first thickness and an outer annular periphery having a second thickness, the second thickness being substantially less than the first thickness, the thickness of the tube gradually diminishing from the inner periphery to the outer periphery.

The method of use of is as follows. The chest is opened to expose the heart, appropriate cannulae are place and cardiopulmonary bypass established using conventional techniques. The left atrium is opened to expose the mitral valve. An appropriate repair procedure to the valve leaflets or chordae is then carried out.

The annuloplasty ring will then be implanted as part of the repair procedure to stabilize the annulus. The appropriate size ring is chosen using sizers supplied for this purpose. Interrupted sutures are placed at the fibrous trigones, between the trigones, and around the remaining circumference of the annulus. The sutures are passed through corresponding portions of the annuloplasty ring, outside the portion containing the spring. The ring is then gently pushed down the sutures until it lies on the annulus. Each interrupted suture is tied and cut. Mitral valve competency is then checked, and if satisfactory the atrium is closed, air is removed from the heart. After the heart starts to beat the patient is slowly removed from cardiopulmonary bypass and the chest closed. Implantation of the tricuspid ring follows a similar course with variations appropriate to the different anatomy.

Incorporated Prior Art
References Cited

United States Patents

| | | | |
|---|---|---|---|
| 3,656,185 | 4/1972 | Carpentier | 3/1.5 |
| 4,042,979 | 8/1977 | Angell | 3/1.5 |
| 4,055,861 | 11/1977 | Carpentier et al. | 3/1.5 |
| 4,164,046 | 8/1979 | Cooley | 3/1.5 |
| 4,217,665 | 8/1980 | Bex et al. | 3/1.5 |
| 4,290,151 | 9/1981 | Massana | 3/1.5 |
| 4,339,831 | 7/1982 | Johnson | 3/1.5 |
| 4,606,911 | 7/1986 | Ahmadi et al. | 623/2 |
| 4,917,698 | 4/1990 | Carpentier et al. | 623/2 |
| 5,450,860 | 8/1993 | O'Connor | 128/898 |

Publications

Tsakiris AG. "The physiology of the mitral valve annulus". in The mitral valve—a pluridisciplinary approach. ed Kalmanson D. Publishing Sciences Group, Acton, Ma., pg 21, 1976.

Geller M, Kronzon I, Slater J et al. "Long-term follow-up after mitral valve reconstruction: incidence of postoperative left ventricular outflow obstruction". Circulation, 74:1–99, 1986.

Carpentier A, Deloche A, Hanania G, et al. Surgical management of acquired tricuspid valve disease. J Thorac Cardiovasc Surg, 67:53, 1974.

Duran CD, and Ubago JLM. "Clinical and Hemodynamic Performance of a Totally Flexible Prosthetic Ring for Atrioventricular Valve Reconstruction" Annals of Thoracic Surgery, 22:458, 1976.

Levine, R. A., Triulzi, M. O., Harrigan P., and Weyman, A. E. "The relationship of mitral annular shape to the diagnosis of mitral valve prolapse", Circulation, 75:756, 1987.

Bex JP and Lecompte Y. "Tricuspid valve repair using a flexible linear reducer", J Cardiac Surg, 1: 151, 1986.

Industrial Application

This invention is useful in the surgical instrument industry.

What is claimed is:

1. An annuloplasty ring comprising: an elongate tube of suturable material, a close coiled biocompatible spring member in said tube, said spring member having first and second ends and defining a passage there through, a string extend through said passage, and means securing the string proximate said ends of said spring for preventing extension of said spring.

2. The annuloplasty ring of claim 1 wherein spring and string are configured and constructed and secured together to define an arc configuration corresponding, in use, to the curved anterior segment of the mitral valve annulus and to permit said arc configuration to vary during the cardiac cycle without extension of said spring.

3. An annuloplasty ring for use in repair a patient's mitral valve annulus, said mitral valve annulus comprising anterior and posterior segments, said annuloplasty ring comprising: an elongate tube of suturable material, a close coiled biocompatible spring member in said tube, said spring member having first and second ends and defining a passage there through, a string extend through said passage, and means securing the string proximate said ends of said spring for preventing extension of said spring, said tube and spring being configured and constructed to encompass, in use, at least a substantial part of the anterior segment of the mitral valve annulus.

4. The annuloplasty ring of claim 3 wherein spring and string are configured and constructed and secured together to define an arc configuration corresponding, in use, to the curved anterior segment of the mitral valve annulus and to permit said arc configuration to vary during the cardiac cycle without extension of said spring.

5. An annuloplasty ring for use in repair a patient's mitral valve annulus, said mitral valve annulus comprising anterior and posterior segments, said annuloplasty ring comprising: an elongate tube of suturable material, a close coiled biocompatible spring member in said tube, said spring member having first and second ends and defining a passage there through, a string extend through said passage, and means securing the string proximate said ends of said spring for preventing extension of said spring, said tube and spring being configured and constructed to encompass, in use, at least a substantial part of the mitral valve annulus.

6. The annuloplasty ring of claim 3 wherein spring and string are configured and constructed and secured together to define an arc configuration corresponding, in use, to the curved anterior segment of the mitral valve annulus and to permit said arc configuration to vary during the cardiac cycle without extension of said spring.

7. An annuloplasty ring comprising: an elongate tube of suturable material, a substantially closely wound helical metallic spring member in said tube, said spring member having first and second ends and defining a passage there through, a string extending through said passage, and means securing the string proximate said ends of said spring for preventing extension of said substantially closely wound helical metallic spring member.

8. The annuloplasty ring of claim 7 wherein said substantially closely wound helical metallic spring member in said tube, said spring member having first and second ends and defining a passage there through defines an arc corresponding, in use, to the curved anterior segment of the mitral valve annulus and to permit said arc to vary during the cardiac cycle without extension of said spring.

9. An annuloplasty ring for use in repair a patient's mitral valve annulus, said mitral valve annulus comprising anterior and posterior segments, said annuloplasty ring comprising:

an elongate tube of suturable material, an elongate tubular flexible, contractile member configured and constructed to define a passage there through in said tube, said elongate tubular flexible contractile member having first and second ends spaced from each other and defining a passage there through, a string extend through said passage, and plugs in the respective spaced first and second ends securing the string proximate said ends of said elongate tubular flexible contractile member for preventing extension of said elongate tubular flexible contractile member, said tube and elongate tubular flexible contractile member being configured and constructed to encompass, in use, a substantial part but not the entirety of the mitral valve annulus.

10. The annuloplasty ring of claim 9 wherein an elongate tubular flexible non-contractile member and string are configured and constructed and secured together to define an arc configuration corresponding, in use, to the curved anterior segment of the mitral valve annulus and to permit said arc configuration to vary during the cardiac cycle without extension of said elongate tubular flexible non-contractile member.

11. An annuloplasty ring for use in the repair of a patient's mitral valve annulus, said mitral valve annulus comprising anterior and posterior segments, said annuloplasty ring comprising: an elongate tube of suturable material, an elongate tubular flexible, contractile member configured and constructed to define a passage there through in said tube, said elongate tubular flexible contractile member having first and second ends spaced from each other and defining a passage there through, a string extend through said passage, and means securing the string proximate said ends of said elongate tubular flexible contractile member for preventing extension of said elongate tubular flexible contractile member, said tube and elongate tubular flexible contractile member comprising suturable expanded polytetrafluoroethylene material configured and constructed to define in cross-section an inner annular periphery having a first thickness and an outer annular periphery having a second thickness, the second thickness being substantially less than the first thickness, the thickness of the tube gradually diminishing from the inner periphery to the outer periphery and being configured and constructed to encompass, in use, a substantial part but not the entirety of the mitral valve annulus.

12. The annuloplasty ring of claim 11 wherein an elongate tubular flexible non-contractile member and string are configured and constructed and secured together to define an arc configuration corresponding, in use, to the curved anterior segment of the mitral valve annulus and to permit said arc configuration to vary during the cardiac cycle without extension of said elongate tubular flexible non-contractile member.

13. An annuloplasty ring for use in repair a patient's mitral valve annulus, said mitral valve annulus comprising anterior and posterior segments, said annuloplasty ring comprising: an elongate tube of suturable material, an elongate tubular flexible, non-contractile member configured and constructed to define a passage there through in said tube, said elongate tubular flexible non-contractile member having first and second ends spaced from each other and defining a passage there through, a string extending through said passage, and means securing the string proximate said ends of said elongate tubular flexible non-contractile member for preventing extension of said elongate tubular flexible non-contractile member, said tube and elongate tubular flexible non-contractile member being configured and constructed to encompass, in use, a substantial part of the anterior segment of the mitral valve annulus, but not to encompass the entire mitral valve annulus, and a thin layer of biocompatible fabric substantially encasing the suturable material to reduce the likelihood that thin layers of tissue may grow there upon and slough off.

14. An annuloplasty ring for use in repair a patient's mitral valve annulus, said mitral valve annulus comprising anterior and posterior segments, said annuloplasty ring comprising: an elongate tube of suturable expanded polytetrafluoroethylene material; and a very thin layer of biocompatible fabric substantially covering said suturable expanded polytetrafluoroethylene material for promoting tissue in growth and reducing the likelihood that thin layers of tissue may grow on the expanded polytetrafluoroethylene and slough off said annuloplasty ring being constructed and configured to define two discrete ends and, in use, to encompass only a substantial portion, and not the entirety, of the mitral annulus.

15. An annuloplasty ring for use in repair a patient's valve annulus comprising: an elongate tube of suturable expanded polytetrafluoroethylene material configured and constructed to define in cross-section an inner annular periphery having a first thickness and an outer annular periphery having a second thickness, the second thickness being substantially less than the first thickness, the thickness of the tube gradually diminishing from the inner periphery to the outer periphery, said annuloplasty ring being constructed and configured to define two discrete ends and, in use, to encompass only a substantial portion, and not the entirety, of the mitral annulus.

* * * * *